(12) United States Patent
Woolverton

(10) Patent No.: US 6,395,288 B1
(45) Date of Patent: May 28, 2002

(54) SUBVERSION OF BACTERIAL RESISTANCE BY LOW SOLUBILITY ANTIBIOTICS

(75) Inventor: Christopher J. Woolverton, Kent, OH (US)

(73) Assignee: Kent State University, Kent, OH (US)

( * ) Notice: Subject to any disclaimer, the term of this patent is extended or adjusted under 35 U.S.C. 154(b) by 102 days.

(21) Appl. No.: 09/064,365

(22) Filed: Apr. 22, 1998

(51) Int. Cl.[7] .................... A01N 25/08; A61K 9/00; A61F 13/00
(52) U.S. Cl. .................. 424/405; 424/400; 424/409; 424/422
(58) Field of Search ................ 424/405, 400, 424/409, 422

(56) References Cited

U.S. PATENT DOCUMENTS 4,997,425 A * 3/1991 Shioya et al. ............... 604/304

OTHER PUBLICATIONS

Greco et al., "Fibrin–Antibiotic Mixtures: An in vitro study assessing the possibility of using a biologic carrier for local drug delivery" *J. Biomed. Materials Res.*, 25:39 (1991).

Thompson et al., "The Addition of Antibiotics of Fibrin Glue" *Southern Medical Journal* 90:681 (1997).

Drohan, "Preparation of Plasma–Derived and Recombinant Human Plasma Proteins" In Hematology: *Basic Principles and Practice,* Churchill Livingston, New York (1994). p. 2019.

Tchao, "Trans–Epithelial Permeability of Fluorescein In Vitro as an Assay to Determine Eye Irritants" *Progress in in vitro Toxicology,* 6:271 (1989).

Barry, "An Improved Single–disk Method for Testing the Antibiotic Susceptibility of Rapidly–growing Pathogens" *Am. Journal of Clinical Pathology,* 53:149 (1970).

Weinstein et al., "Experimental Intra–Abdominal Abscesses in Rats: Development of an Experimental Model" *Infection and Immunity,* 10:1250 (1974).

C.J. Woolverton et al. "Antibiotic Release from Fibrin Sealant", (1997), pp. 3–4, Biological Science.

* cited by examiner

*Primary Examiner*—Shelley A. Dodson
(74) *Attorney, Agent, or Firm*—Renner, Kenner, Greive, Bobak, Taylor & Weber

(57) ABSTRACT

A site-specific antibiotic delivery system and related method comprising a fibrin sealant and an antibiotic releasably bound to the fibrin sealant, wherein the antibiotic is delivered in situ and wherein the dose of antibiotic delivered to the organism is sufficient to kill substantially all antibiotic-resistant bacteria present in an infectious focus.

18 Claims, 4 Drawing Sheets

SUBVERSION OF BACTERIAL RESISTANCE BY LOW SOLUBILITY ANTIBIOTICS

TECHNICAL FIELD

This invention generally relates to a site-specific antibiotic delivery system. More particularly, the present invention relates to a system that uses a carrier, such as a fibrin sealant, to deliver one or more antibiotics in situ. Specifically, the present invention relates to a system that can deliver a dose of antibiotics sufficiently high to overcome antibiotic-resistant bacteria.

BACKGROUND OF THE INVENTION

Infection is the presence and successful multiplication of a microbe, such as a bacterium, virus, fungus or parasite, on or within a host or patient. An infection begins at a local nidus, or focal point, and typically results in local cellular injury due to toxins, competition for nutrients, intracellular replication, or a combination thereof. Once local cellular injury begins, the infected area is deemed an "infectious focus." Few antibiotics exhibit truly selective toxicity (i.e., only toxic to bacterial cells) and therefore result in side effects to the patient.

Side effects such as allergy, renal or hepatic injury, nerve cell damage, hypotension and neutropenia are common during the systemic use of antibiotics and thus limit the dose of antibiotics that can be used to treat the infection. These side effects are often due not only to a lack of selective toxicity, but also to the systemic absorption of the drug.

Since the 1940s, bacterial infections have been very successfully treated with antibiotics. In recent years, however, infection by multi-drug resistant (MDR) bacteria has been a growing problem. It is clear that the natural selection of antibiotic-resistant bacteria has resulted from excessive, prolonged and indiscriminate use of antibiotics, as well as over-the-counter availability, resulting in the increasing occurrence of infection by antibiotic-resistant bacteria. Increased antibiotic prophylaxis, the use of broad-spectrum agents and the poor education of patients and prescribers regarding the need and use of antibiotics have compounded the problem. For purposes of this specification, "MDR," "resistant," and "antibiotic resistant" bacteria refer to those bacteria so classified by federal testing agencies and as understood by one of ordinary skill in the art.

While there are numerous individual mechanisms, in general, antibiotics damage bacteria via discrete interaction with structural components or metabolic pathways. The biochemical mechanisms by which bacteria resist antibiotic activity may include prevention of drug entry into the cell, rapid extrusion of the drug from the cell, enzymatic inactivation of the drug or alteration of the molecular target. Also participating in the increasing resistance are the so-called "non-canonical mechanisms" of gene dosage, heterologous induction, population resistance and low resistance synergism.

Current attempts to control infection by antibiotic-resistant bacteria include multiple-antibiotic therapies, supplementation of antibiotics with resistance inhibitors, immune modulating drugs, or combinations thereof. In many cases, systemic antibiotic concentrations exceed recommended levels, resulting in host toxicity.

Local therapy has some advantages over systemic therapy. First, as discussed, selective toxicity may not be achieved with conventional treatment. Second, systemic drug delivery may be unnecessary, unsafe or contraindicated. Third, the maximum tolerable systemic dose of antimicrobial agent may not be efficacious due to poor vascularization, chronicity of infection or, more importantly, resistant microbes.

For purposes of this specification, "host toxicity," "whole animal toxicity," or merely "toxicity" refers to the subjective evaluation of the overall health of a patient as commonly known and understood by one of ordinary skill in the art. "Low toxicity" or "substantially non-toxic" means there are no or only minor side effects, as determined, for example, by phase I studies. By contrast, "cellular toxicity" refers to injury to cells, such as measured by a fluorescein assay.

Fibrin sealant has several unique characteristics which make it suitable as a delivery matrix for pharmaceuticals, such as antibiotics, in a patient. First, fibrin sealant is hemostatic, i.e., reduces bleeding, which may facilitate healing. Second, the cross linked fibrin monomers of fibrin sealant create pores of proper size to trap and then release various pharmaceutical compounds. Third, release of trapped compounds is governed by a diffusion-dissolution mechanism, whereby the compound slowly dissolves when it is within the fibrin sealant matrix and also when it is released during the natural fibrinolysis process. For example, fibrin sealant has been used to deliver demineralized bone and bone morphogenetic proteins to repair bone defects in rats, to deliver acidic fibroblast growth factor-1 to Teflon shunts for endothelial cell recruitment forming artificial vascular grafts in dogs, to deliver antiproliferative chemotherapeutic agents in a mouse model of human ovarian cancer and to deliver antibiotics to treat infection. Commercial laboratories manufacture fibrin sealant components primarily for homoeostasis, such as the treatment of large surface area wounds in clotting-factor-deficient victims and the sealing of post-operative micro vascular leakage.

Antibiotic-supplemented fibrin sealant is also known. Greco et al., J. Biomed. Materials Res., 25:39 (1991), for example, discloses that antibiotics were found to be almost completely released by 96 hours, the greatest percentage of material (greater than 85 percent) having been released within 72 hours. Release of antibiotics over this relatively short time period most likely resulted from the rapid diffusion of small ionic molecules designed for maximum absorption during oral and parenteral delivery of a clinical formulation. This rapid release from fibrin sealant is clinically unacceptable when a longer course of treatment is required.

It is also known that a low dose of low-solubility antibiotics can be released from fibrin sealant to kill non-resistant bacteria. "Low solubility," as used herein, refers to a species that one of ordinary skill in the art would describe as having a low solubility in water. Typically, such compounds are described in the Merck Index as "poorly soluble," "practically insoluble," "slightly soluble," "sparingly soluble," etc. Generally, such compounds have a solubility less than about 2 mg/mL at room temperature. Preferably, such compounds have a solubility less than about 1 mg/mL.

A need remains for a formulation and method that will deliver a high dose of antibiotic that can overcome antibiotic-resistant bacteria with low host toxicity. Heretofore, the prior art cast serious doubt on the feasibility of such a formulation. First, Greco et al. and Thompson et al., *Southern Medical J.* 90:681 (1997), teach that increasing the loading dose of antibiotic onto fibrin sealant slows coagulation by interfering with the formation of fiber from fibrinogen. Second, heretofore it was uncertain whether the host toxicity could be kept low upon the administration of an effective high dose of antibiotic.

SUMMARY OF INVENTION

It is therefore an object of the present invention to provide a site-specific antibiotic delivery system.

It is another object to provide a fibrin-antibiotic delivery system such that the antibiotic releases from the fibrin in high concentrations in vivo.

It is yet another object of the present invention to provide a system that will deliver antibiotics in a dose sufficient to kill antibiotic-resistant bacteria.

It is another object of the present invention to provide a method for the site-specific delivery of antibiotics.

At least one or more of the foregoing objects, together with the advantages thereof over the known art relating to antibiotic delivery systems, which shall become apparent from the specification which follows, are accomplished by the invention as hereinafter described and claimed.

In general, the present invention provides a method of delivering a high dose of antibiotic comprising the step of inserting an antibiotic releasably bound to a carrier into an organism wherein the antibiotic is delivered in situ, wherein the dose of antibiotic delivered to the organism is sufficient to kill substantially all antibiotic-resistant bacteria present in an infectious focus.

The present invention also provides a site-specific antibiotic delivery system comprising a carrier and an antibiotic releasably bound to the carrier, wherein the antibiotic is delivered in situ and wherein the dose of antibiotic delivered to the organism is sufficient to kill substantially all antibiotic-resistant bacteria present in an infectious focus.

PREFERRED EMBODIMENT

Figure 1A:
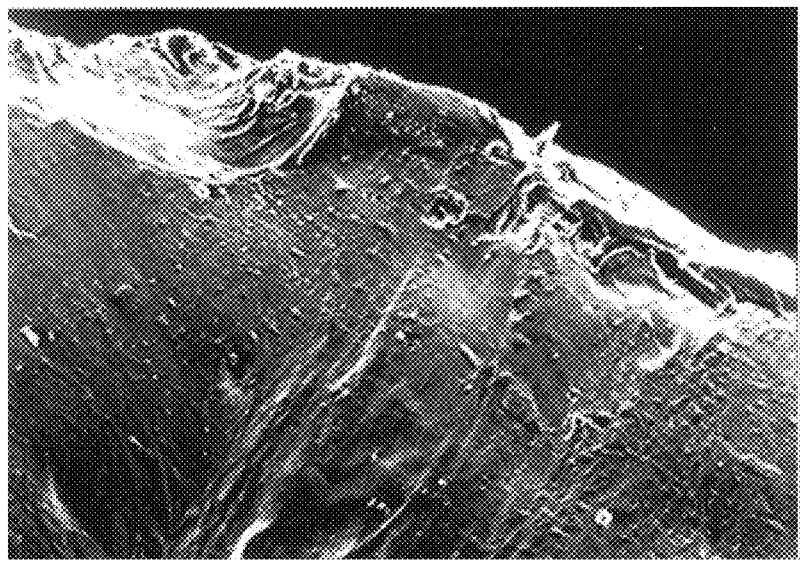
FIG. 1a is a scanning electron micrograph of a portion of a fibrin sealant magnified 170 times.
Figure 1B:
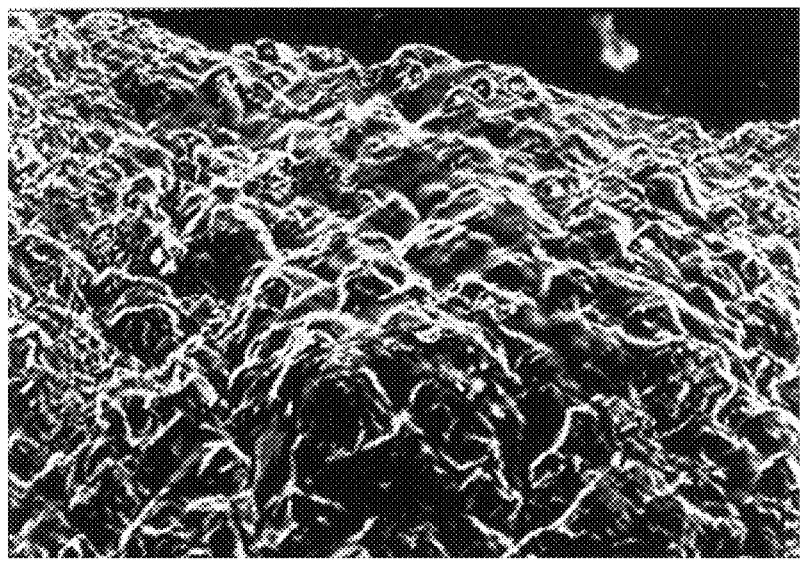
FIG. 1b is a scanning electron micrograph of the fibrin sealant of FIG. 1a having the antibiotic tetracycline free base (TET) embedded therein and magnified 170 times.
Figure 1C:
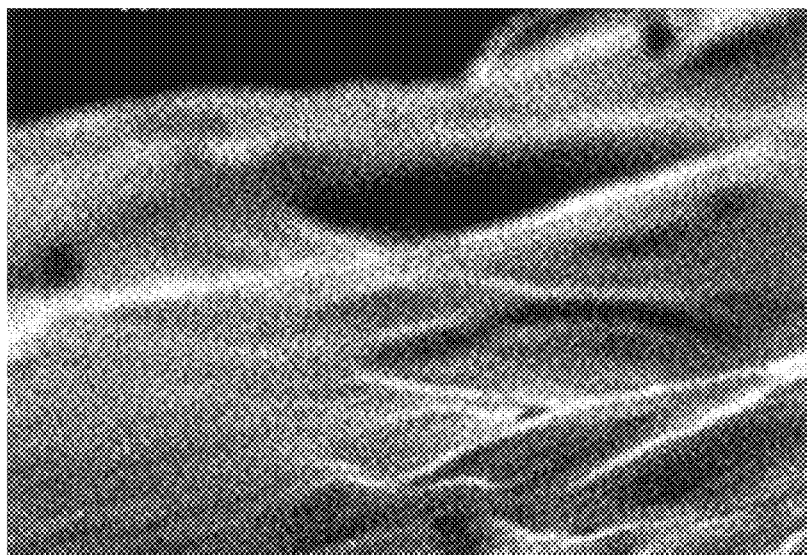
FIG. 1c is a scanning electron micrograph of a portion of the fibrin sealant of FIG. 1a magnified 5500 times.
Figure 1D:
FIG. 1d is a scanning electron micrograph of a portion of the fibrin sealant of 1a having the antibiotic tetracycline free base (TET) embedded therein and magnified 5500 times.

It has now been found that direct exposure of antibiotic-resistant bacteria to an overwhelming local dose of one or more conventional antibiotics may overcome one or more mechanisms of resistance and facilitate bacterial eradication. In addition, a method has been developed to deliver a high dose of antibiotic over a period of time sufficient to kill antibiotic-resistant bacteria with low toxicity to a patient.

The present invention is efficacious and cost effective because many low solubility, synthetic antibiotic forms are cheaper precursor products which have not been used clinically. In addition, the cost of antibiotic delivery concurrent with wound debridgement, culture acquisition or tissue management would be minimal compared with the cost associated with repeated surgery, a prolonged hospital stay, or an additional nosocomial infection.

Specifically, it has now been found that antibiotic-resistant bacteria can be killed using a carrier that releases a quantity of antibiotic over a long period of time sufficiently large to exceed the minimal inhibitory concentration (MIC) of the bacteria. Local delivery of an antibiotic to the focal site of infection may result in a higher therapeutic index—the ratio of the highest non-toxic dose to the MIC required to control a microbe—and fewer systemic side effects. Preferably, the carrier is a natural or synthetic polymer that can slowly release an antibiotic without causing harm to the patient. Accordingly, the carrier releasably binds or encapsulates an antibiotic and has pores that are big enough to allow the antibiotic to diffuse out, but small enough that the diffusion is slow. In addition, the carrier is preferably biodegradable in vivo, but does so sufficiently slowly to allow long-term delivery of the antibiotic. The carrier preferably has pores ranging from about 1 to about 10 microns in diameter. A highly preferred carrier is a fibrin sealant, which consists of cross-linked monomers.

As used herein, a "high dose" of antibiotic refers to the size of a single bolus in a carrier disposed in a patient such that the carrier releases the antibiotics at a rate sufficient to maintain a local concentration of antibiotic greater than or equal to the MIC of the resistant bacteria of an infectious focus and such that the size of the bolus is sufficient to maintain the rate of delivery until substantially all of the bacteria are killed and the infectious focus is overcome.

Fibrin sealant is typically made of fibrinogen, thrombin and Factor XIII isolated from fractionated human plasma and treated to neutralize or remove microorganisms such as enveloped viruses. Fibrin sealant is the result of fibrin monomers that are converted from purified fibrinogen by the enzyme thrombin and cross-linked by Factor XIII. The manufacture of fibrin sealant is described by Drohan, *In Hematology: Basic Principles and Practice,* Churchill Livingston, New York (1994), p. 2019, incorporated herein by reference, and is also commercially available.

One or more antibiotics are applied to the matrix such that the antibiotic molecules become entrapped in the pores of the matrix. Use of relatively low solubility antibiotics generally increases the antibiotic effectiveness by decreasing the rapidity of release from the fibrin carrier and by increasing the local antibiotic concentration and exposure time, typically from about 1 to 3 weeks. Unlike a soluble antibiotic, a relatively insoluble one does not readily move or disperse. Furthermore, local delivery of low solubility antibiotics results in minimal systemic load and therefore minimal selective pressure on commensal microorganisms distal to the infectious focus. This is important in preventing the proliferation of resistant microorganisms and in preventing harm to beneficial microorganisms found in the body. Examples of suitable antibiotics which are poorly soluble in aqueous buffer systems include, but are not limited to, tetracycline free base (TET), streptomycin (STR), penicillin G (PEN-G), penicillin O, sulfamethoxazole-trimethoprim (SXT), norfloxicin (NOR), streptolydigin, rifamycin X, cefoxitin, and pipemidic acid. A highly preferred delivery system is biocompatible, resorbable, easy to use, inexpensive and releases efficacious amounts of drug over a predetermined time frame.

Choice of the most appropriate antibiotic is dependent upon factors such as the site of infection, the degree of antibiotic penetration into the site, the infecting bacterium, and the relative toxicity to the host. Narrow spectrum antibiotics should be used whenever possible because they exhibit the most selective toxicity toward the infecting microbe. However, the carefully standardized in vitro test results do not always correlate with the in vivo situation, where antibiotic effectiveness is altered by drug penetration and host immune response.

Fibrin sealant can be prepared with antibiotic embedded therein either in in vitro (and surgically implanted) or in situ. It is envisioned that the fibrin sealant disks will generally be implanted at the specific infection site to control local disease. The anticipated use of the present invention is primarily therapeutic, i.e., after an infectious focus is discovered. But the present invention can also be used prophylactically, i.e., by inserting the antibiotics into a patient before an infectious focus is discovered.

The quantity of antibiotic delivered to the patient kills substantially all antibiotic-resistant bacteria present in an infectious focus. Preferably, the quantity of loaded antibiotics is sufficiently high that the amount delivered in situ exceeds the saturation level of the physiological environment at the infectious focus. Accordingly, the undissolved antibiotic is less prone to leave the focus. Preferably, the concentration of the antibiotic in situ is maintained at a level greater than or equal to the MIC for the bacteria until substantially all of the bacteria are killed. While systemic antibiotic delivery generally requires a course of treatment of 7–10 days, it is believed that the present invention will need a shorter course of treatment, perhaps as little as 2–3 days.

Antibiotic efficacy results when the drug exhibits effective and selective toxicity on the invading bacteria. However, typical dose escalation required to control MDR infections results in significant, negative side-effects to the host. Therefore, to evaluate drug efficacy, the therapeutic index is calculated as the highest dose without host toxicity divided by the MIC. The proposed invention redefines the numerator of the fraction since relatively larger doses of less soluble antibiotic, sequestered within the carrier, are slowly released with time, posing minimal toxicity to the host. Preferably, the therapeutic index is greater than 10 and may be as high as 100 or more, but will be dependent on individual drug release kinetics.

Under typical physiological conditions (pH 7.4, 37° C., bathed in aqueous fluid), the antibiotic molecules are released from fibrin sealant by a diffusion-dissolution mechanism. Initially, a limited number of antibiotic molecules dissolve in their aqueous environment in vivo. Meanwhile, the fibrin slowly breaks down by a natural fibrinolysis process, thereby increasing the surface area of the fibrin particles and exposing more antibiotic molecules to the aqueous environment. FIG. 1 shows scanning electron micrographs of fibrin sealant bound to TET (FS-TET).

In situ antibiotic therapy is most preferred when the antibiotic delivery kinetics can be precisely regulated, the antibiotic exerts minimal local and systemic toxicity, the infection is suitably contained in one or few locations, and the local antibiotic concentration is significantly greater than the MIC, saturating pre-formed resistance factors and effectively inhibiting bacterial growth. It is contemplated that local antibiotic therapy would be effective in treatment concurrent with invasive procedures already required for patient management, such as surgical debridgement, culture acquisition, or exploratory investigation. Other uses include minimally invasive procedures, such as delivery via endoscopy, and in conjunction with open or chronically infected sites, such as in osteomyelitis or periodontitis.

Experimental

An antibiotic was embedded in a fibrin sealant by mixing. Typically, an antibiotic is dissolved or suspended in a 133 mg/ml aqueous fibrinogen solution that contains 24 μg/ml Factor XIIIa. Prior to mixing with a solution of thrombin (330 Iu/ml) and calcium chloride (40 mmol/L), the antibiotic-fibrinogen solution is twice the desired final concentration. Alternatively, all dry materials may be admixed and hydrated at a later time period. The above materials may be mixed in vitro to generate the antibiotic-embedded fibrin matrix or in vivo through a dual-lumen syringe. The embedded fibrin sealant produced in vitro can then be washed with a solution such as 0.9% phosphate-buffered saline. The embedded fibrin sealant is then ready to be used in vivo.

Earlier studies by Woolverton et al. (unpublished) showed that prophylactic treatment of only 500 mg/kg tetracycline was required to provide 100% protection against a lethal dose of non-multi-drug resistant (NMDR) peritonitis in mice.

Local (cellular) toxicity of two forms of TET in vitro was evaluated using a fluorescein assay, as described by Tchao, *Progress in in vitro Toxicology*, 6:271 (1989), incorporated herein by reference. FS-TET disks of TET-HCl (20 mg/mL) or TET free base (1 mg/mL), their respective solubility limits, showed that the more soluble TET-HCl was acutely toxic, but the less soluble TET free base was nontoxic.

The duration of the prophylactic effect of FS-TET against NMDR *Staphylococcus aureus* (*S. aureus*) was maximized using a dose of 1750 mg/kg TET. This dose produced 100% survival in mice when implanted 35 days before injection of bacteria causing lethal peritonitis.

Figure 2:
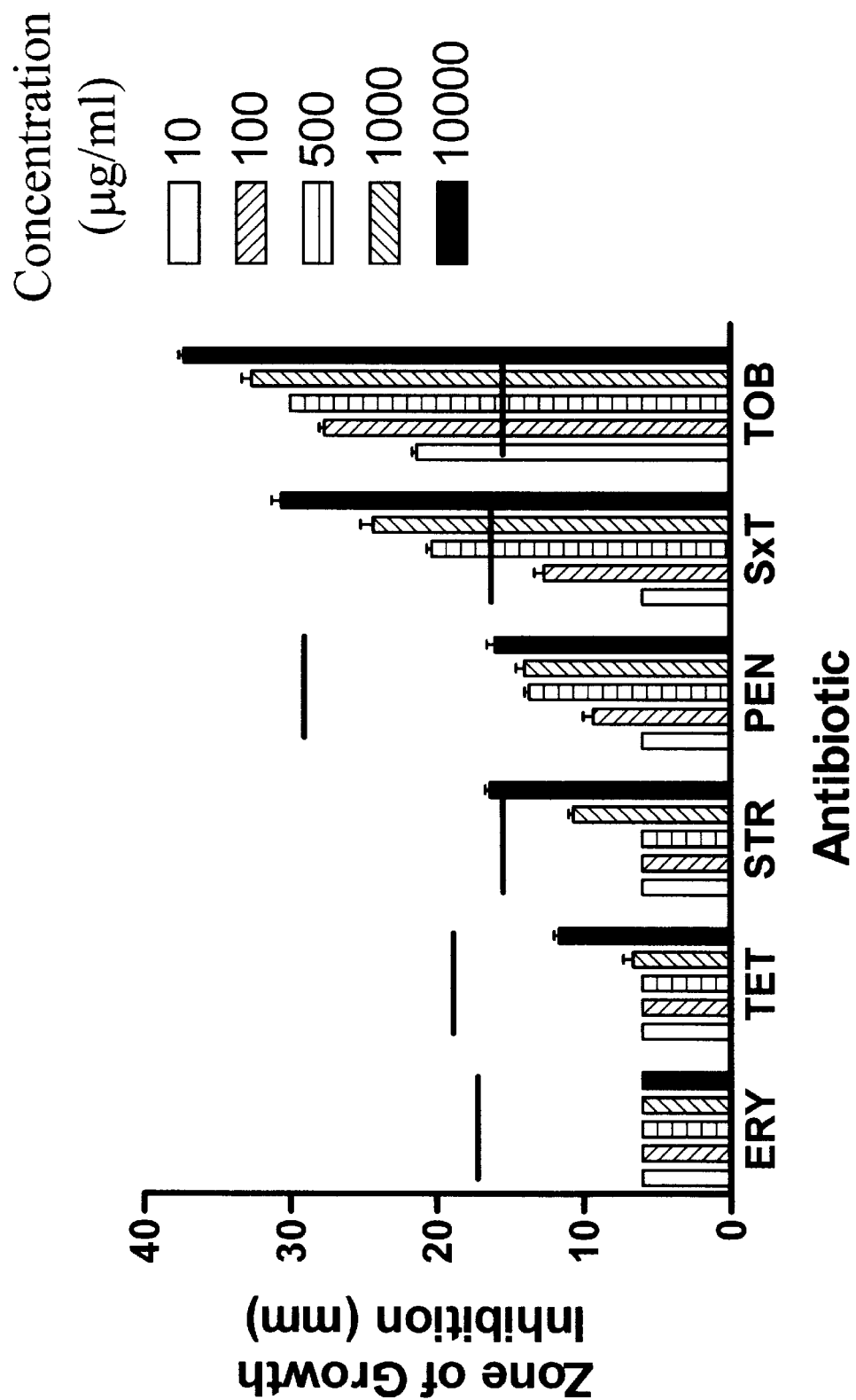
FIG. 2 is a bar graph representation of the in vitro results of the zone of growth inhibition (mm) for six representative antibiotics at various increasing local concentrations ($\mu$g/mL).

Data using a MDR isotype of *S. aureus* (ATCC 27659) demonstrate that delivery of antibiotics from fibrin sealant in vitro results in dose-dependent growth inhibition (FIG. 2). The method used was that of Barry,*Am. Journal of Clinical Pathology*, 53:149 (1970), incorporated herein by reference, with modifications. Briefly, antibiotic bioactivity was assessed by agar diffusion where the agar hydrogel was seeded with bacteria prior to solidification. Several 6 mm wells were cut into the agar, the plugs were removed by aspiration and the wells were filled with the fibrin sealant hydrogel containing various concentrations of low-solubility antibiotics. Cultures were incubated for 18 h at 37° C. Zones of growth inhibition—the area about the well where diffused antibiotic prevents growth of seeded bacteria—were recorded to the nearest mm and graphed in FIG. 2. The zone of inhibition required to document bacterial susceptibility to a particular concentration of antibiotic is indicated by a black horizontal bar. The data of FIG. 2 clearly demonstrate that the low solubility antibiotics were delivered from fibrin sealant as bioactive. Moreover, increasing the local concentration of low solubility antibiotics released from fibrin sealant effectively overcomes *S. aureus* resistance in vitro.

Figure 3:
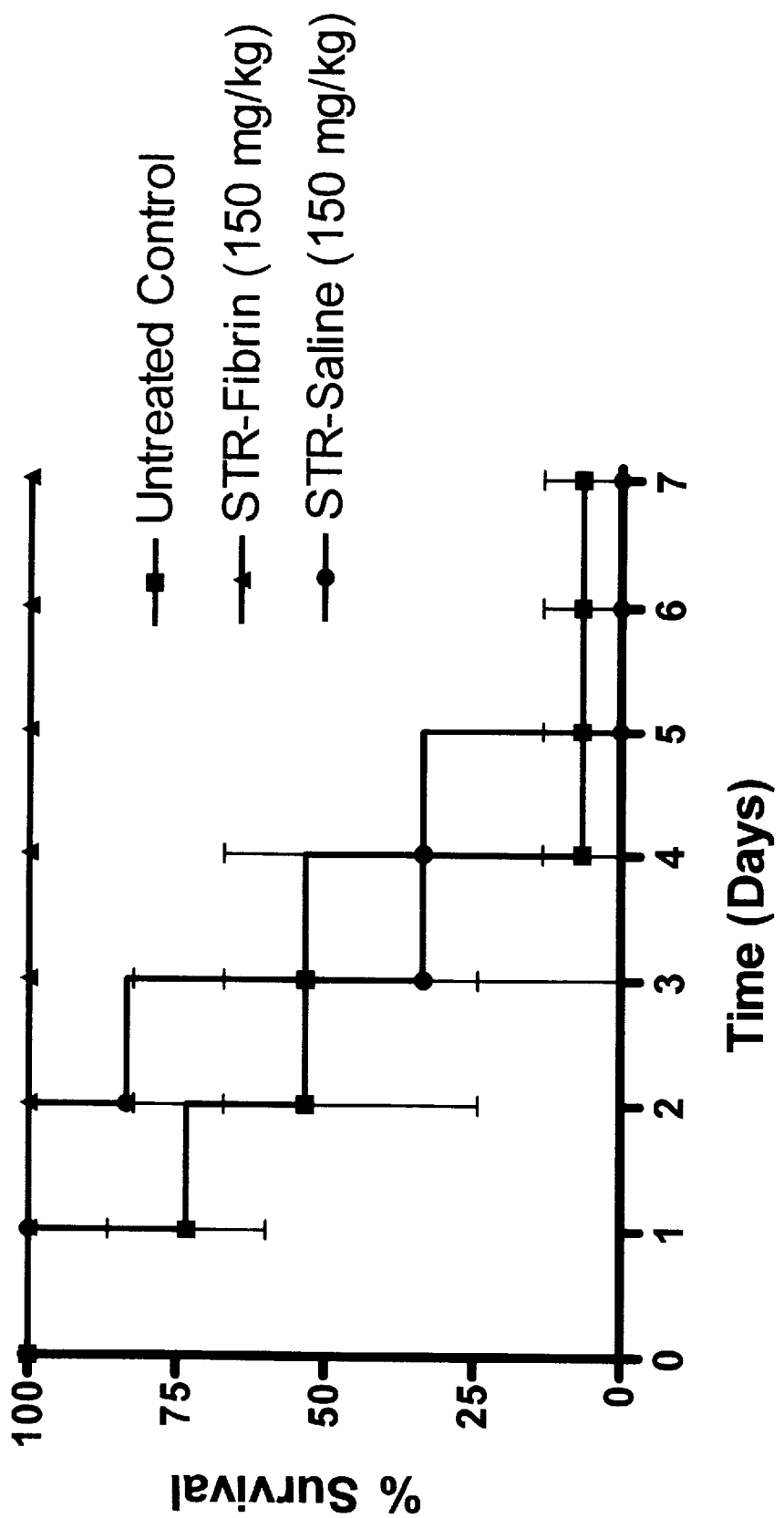
FIG. 3 is a graphical comparison of the percent of survival of test animals left untreated, or given a high dose of the antibiotic streptomycin (150 mg/kg) carried by saline or carried by a fibrin sealant implanted at a specific site within the animal to treat intra-abdominal sepsis.

These data are supported in vivo, as well. Using the method of Weinstein et al.,*Infection and Immunity*, 10:1250 (1974), incorporated herein by reference, intra-abdominal sepsis was initiated in Fisher 344 rats with the MDR *S. aureus*. Since streptomycin appeared effective in vitro, sepsis was initiated and followed 30 minutes later with a single intra peritoneal injection of 150 mg/kg streptomycin in fibrin sealant or in saline. As shown in FIG. 3, rats administered streptomycin in fibrin sealant survived sepsis initiated by MDR *S. aureus*. Rats administered streptomycin in saline did not survive, with mortality rates resembling untreated controls.

Thus it should be evident that the system and methods of the present invention are highly effective in treating bacterial infection. The invention is particularly suited for treating multi-drug resistant bacteria, but is not necessarily limited thereto. The system and method of the present invention can be used separately with other antibiotics, methods and the like.

Based upon the foregoing disclosure, it should now be apparent that the use of the delivery system described herein will carry out the objects set forth hereinabove. It is, therefore, to be understood that any variations evident fall within the scope of the claimed invention and thus, the selection of specific component elements can be determined without departing from the spirit of the invention herein disclosed and described. Thus, the scope of the invention shall include all modifications and variations that may fall within the scope of the attached claims.

What is claimed is:

1. A method for delivering to a patient a high dose of at least one low solubility antibiotic to an in vivo site containing antibiotic-resistant bacteria comprising:
   embedding the high dose of the at least one low solubility antibiotic in a carrier; and placing the carrier at the in vivo site,
   wherein the carrier releases the at least one low solubility antibiotic in situ at a rate and for a duration effective to kill substantially all antibiotic-resistant bacteria present in the in vivo site.

2. The method according to claim 1, wherein the antibiotic-resistant bacteria are concentrated at an infectious focus within the site.

3. The method according to claim 1, wherein the at least one low solubitiy antibiotic is substantially non-toxic to the patient.

4. The method according to claim 1, wherein the carrier is a fibrin sealant.

5. The method according to claim 1, wherein the carrier releases the at least one low solubility antibiotic in situ in a quantity that exceeds a saturation level of at least a portion of the in vivo site.

6. The method according to claim 5, herein the portion of the in vivo site includes an infectious focus.

7. The method according to claim 1, wherein delivery of the at least one low solubility antibiotic results in a therapeutic index greater than 10.

8. The method according to claim 1, wherein the step of placing includes inserting the carrier into an infectious focus.

9. The method according to claim 1, wherein the step of placing includes implanting the carrier into the patient.

10. A method for delivering to a patient a high dose of at least one low solubility antibiotic to an in vivo site containing antibiotic-resistant bacteria comprising:
    embedding the high dose of the at least one low solubility antibiotic in a carrier; and placing the carrier at the in vivo site, wherein the carrier releases at least one low solubility antibiotic in situ in a quantity that exceeds a saturation level of at least a portion of the in in vivo site over the course of at least 7 days to kill substantially all antibiotic-resistant bacteria present in the in vivo site.

11. An article suitable for delivering to a patient at least one low solubility antibiotic to a site containing antibiotic-resistant bacteria comprising:
    a fibrin sealant; and
    a high dose of at least one low solubility antibiotic releasably carried by the fibrin sealant wherein the fibrin sealant releases the at least one solubility antibiotic in sits at a rate and for a duration effective to kill substantially all antibiotic-resistant bacteria present in the site.

12. The article according to claim 11, wherein the fibrin sealant releases the at least one low solubility antibiotic in situ in a quantity that exceeds a saturation level of at least a portion of the site.

13. The article according to claim 11, wherein the at least one antibiotic is substantially non-toxic to the patient.

14. The article according to claim 11, wherein delivery of the at least one low solubility antibiotic results in a therapeutic index greater than 10.

15. A method for killing antibiotic-resistant bacteria present in an infectious focus of a patient comprising:
    delivering in situ a carrier embedded with at least one low solubility antibiotic to the infectious focus in a dose that is substantially non-toxic to the patient and in a concentration equal to or greater than a minimum inhibitory concentration for the antibiotic-resistant bacteria; and
    maintaining the concentration for a period of time sufficient to kill the antibiotic-resistant bacteria.

16. The method according to claim 15, wherein the period of time is at least 2 days.

17. The method according to claim 15, wherein the carrier is a fibrin sealant.

18. The method according to claim 1 where in the at least one low solubility antibiotic is selected from the group consisting of tetracycline free base, streptomycin, penicillin G, penicillin O, sulfamethoxazole-trimethoprim, norfloxicin, streptolydigin, rifamycin X, cefoxitin, and pipemidic acid.

* * * * *

UNITED STATES PATENT AND TRADEMARK OFFICE
CERTIFICATE OF CORRECTION

PATENT NO. : 6,395,288 B1
DATED : May 28, 2002
INVENTOR(S) : Woolverton

It is certified that error appears in the above-identified patent and that said Letters Patent is hereby corrected as shown below:

<u>Column 7,</u>
Line 42, "herein" should read -- wherein --.

<u>Column 8,</u>
Line 17, "in sits" should read -- in situ --.

Signed and Sealed this

Eleventh Day of November, 2003

JAMES E. ROGAN
*Director of the United States Patent and Trademark Office*